United States Patent [19]
Hodorek

[11] Patent Number: 5,534,027
[45] Date of Patent: Jul. 9, 1996

[54] METHOD FOR PROVIDING A BARRIER TO THE ADVANCEMENT OF WEAR DEBRIS IN AN ORTHOPAEDIC IMPLANT ASSEMBLY

[75] Inventor: Robert A. Hodorek, Warsaw, Ind.

[73] Assignee: Zimmer, Inc., Warsaw, Ind.

[21] Appl. No.: 342,279

[22] Filed: Nov. 18, 1994

Related U.S. Application Data

[62] Division of Ser. No. 80,265, Jun. 21, 1993, abandoned.

[51] Int. Cl.$^6$ .............................. A61F 2/28; A61B 17/86
[52] U.S. Cl. .................................. 623/16; 623/18; 606/69
[58] Field of Search .................... 623/16, 18; 606/69–71

[56] References Cited

U.S. PATENT DOCUMENTS

| | | | |
|---|---|---|---|
| 1,179,136 | 4/1916 | Ollis .................................... | 411/380 X |
| 1,868,084 | 7/1932 | Wheelwright ......................... | 403/77 x |
| 2,007,179 | 7/1935 | Bullis . | |
| 3,329,454 | 7/1967 | Melton et al. ............................ | 403/77 |
| 3,342,513 | 9/1967 | Melton et al. ........................ | 403/77 X |
| 3,441,300 | 4/1969 | Ho ....................................... | 403/77 x |
| 3,882,752 | 5/1975 | Gutshall . | |
| 4,235,147 | 11/1980 | Weidner ............................ | 411/542 X |
| 4,310,273 | 1/1982 | Kirrish ............................... | 411/542 X |
| 4,511,276 | 4/1985 | Doult ......................................... | 403/77 |
| 4,577,450 | 3/1986 | Large . | |
| 4,705,520 | 11/1987 | Ahrens ...................................... | 623/23 |
| 4,794,918 | 1/1989 | Wolter ..................................... | 606/69 |
| 4,875,474 | 10/1989 | Border . | |
| 5,040,982 | 8/1991 | Stefan-Dogar ......................... | 433/169 |
| 5,125,839 | 6/1992 | Ingber et al. ............................ | 433/169 |
| 5,127,914 | 7/1992 | Calderale et al. ....................... | 606/65 |
| 5,163,960 | 11/1992 | Bonutti .................................... | 623/16 |
| 5,209,751 | 5/1993 | Farris et al. .............................. | 606/61 |
| 5,217,498 | 6/1993 | Henssge et al. ......................... | 623/20 |
| 5,269,784 | 12/1993 | Mast ......................................... | 606/69 |

FOREIGN PATENT DOCUMENTS

| | | | |
|---|---|---|---|
| 2114323 | 10/1971 | Germany ................................. | 623/18 |
| 1517823 | 7/1978 | United Kingdom ................... | 411/379 |
| 88/03781 | 6/1988 | WIPO ..................................... | 606/70 |

OTHER PUBLICATIONS

Zimmer, Inc. brochure—"Acetabular Implant Systems" — 1985, 1988.

Zimmer, Inc. brochure — "MG II Total Knee System" — 1992.

Zimmer, Inc. brochure — "Versa–FX Femoral Fixation System" — 1991.

*Primary Examiner*—David H. Willse
*Attorney, Agent, or Firm*—Margaret L. Geringer

[57] ABSTRACT

An orthopaedic implant assembly 1 including a securing member or screw 10 and sealing washer 20 assembled thereto. The assembly 1 further includes a base member 30 with a hole 31 therein for receiving the screw 10 and washer 20. The screw 10 includes an enlarged head 11 with an arcuate undersurface 14 with a groove surrounding head 11 for receiving the sealing washer 20 therein. The screw hole 31 includes a complementary arcuate surface to enable screw 10 to be inserted in a selectively variable angled orientation with respect to the screw hole 31 while the washer 20 provides a seal between the head 11 of screw 10 and the base member 30. The assembly 1 may further include an additional member 40 over the hole 31 and screw 10 and washer 20, such that this layer 40 generates wear debris. The sealing washer 20 provides a barrier to the advancement of the wear debris or particulate matter beyond the sealing washer 20.

4 Claims, 3 Drawing Sheets

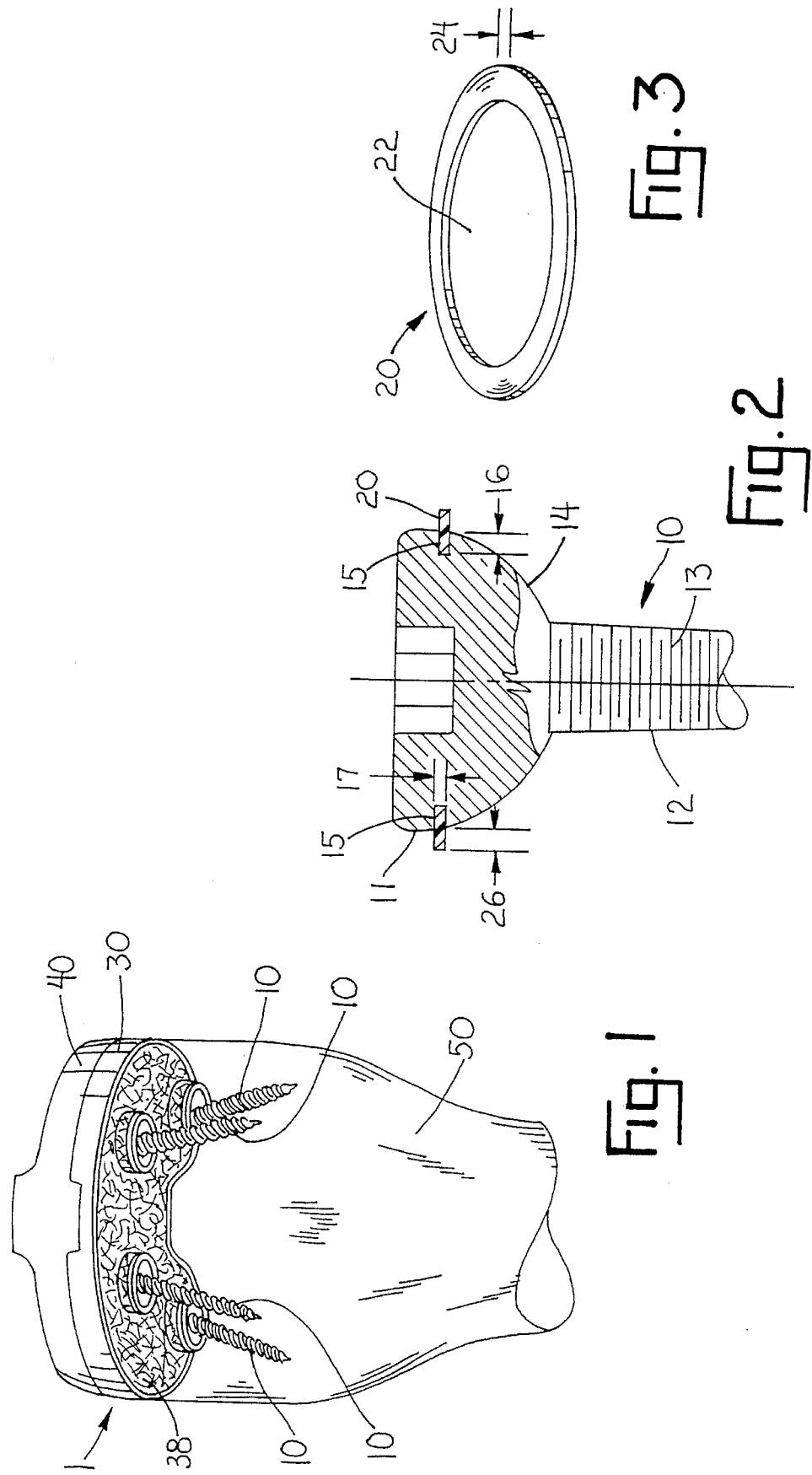

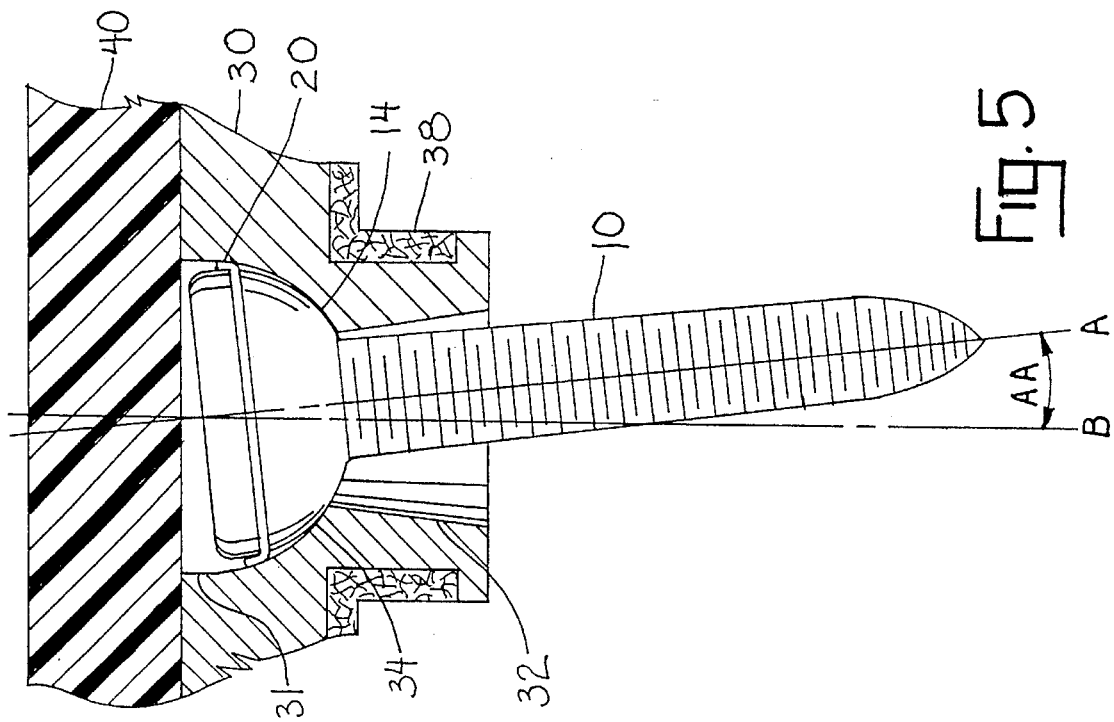
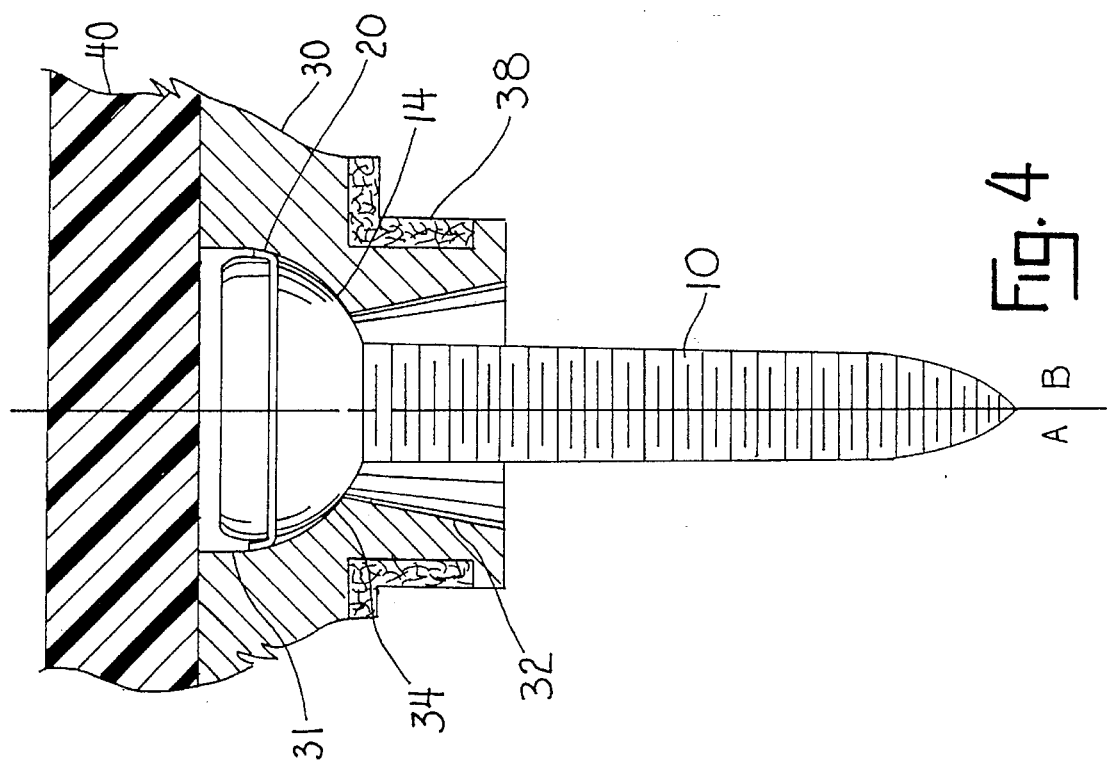

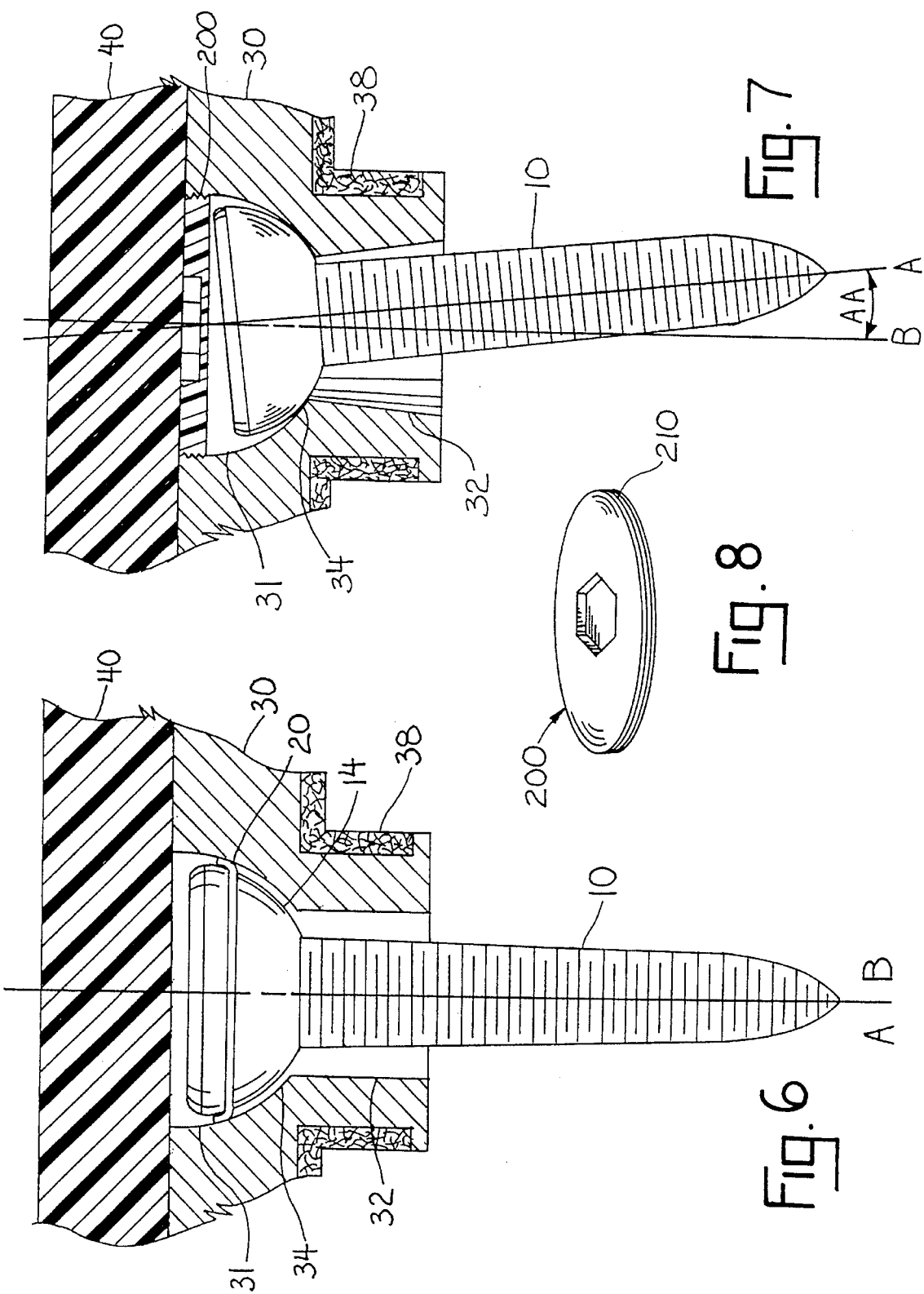

5,534,027

METHOD FOR PROVIDING A BARRIER TO THE ADVANCEMENT OF WEAR DEBRIS IN AN ORTHOPAEDIC IMPLANT ASSEMBLY

This is division of application Ser. No. 08/080,265 filed Jun. 21, 1993, now abandoned.

FIELD OF INVENTION

This invention relates to the field of orthopaedic implant assemblies. In particular, this invention relates to such implant devices in which at least one component is assembled or secured with at least one securing member, such as a screw, and as such, relates to the provision of a seal between the securing member and the component.

BACKGROUND OF THE INVENTION

In the field of orthopaedics, it is well known to secure various types of implant components with screws. For example, a prosthetic hip cup may include a hemi-spherical shaped outer metal shell which is screwed into the prepared acetabulum. An inner mating articulating surface (often made of a plastic such as ultra high molecular weight polyethylene, UHMWPE) is then secured to this outer shell. A prosthetic femoral hip stem then typically mates with this inner articulating surface of the hip cup. Alternatively, the tibial component of a prosthetic knee joint may include a metal support plate which is screwed on to the prepared proximal tibia. A mating tibial articulating surface, which again may be UHMWPE, is then secured to the support plate. A prosthetic femoral knee component then typically mates with this tibial articulating surface.

It has been discovered that over time particulate matter or wear debris may be generated from the articulation of this prosthetic load bearing joint, and that this particulate may pass beneath the UHMWPE articular surface and move down along the screw head and shaft causing bone lysis. It is known to provide polyethylene plugs to block the screw hole openings in base members such as tibial plates if screws are not utilized through such holes to prevent the particulate from passing through the holes. However, if the screws are used, the plugs are removed and then the particulate may then pass through the hole and move down along the screw.

In other implants, screws may be utilized to either secure components to bone, such as with bone plates, or to secure directly to the implant component, such as in U.S. Pat. No. 4,875,474 to Border in which an end cap is threadedly secured to an intramedullary nail. Border discloses a seal or washer 264 shown in FIG. 12 and described at column 7, lines 19–24 and 50–56. The washer 264 is provided to form a seal between the bottom surface of head 266 of end cap 260 and the end of proximal portion 212 of the nail. This seal is indicated to prevent the ingrowth of tissue (into the opening in the nail) during the implantation period. The seal of Border is beneath the flat surface of the head of the end cap, and is limited to the axis of the shaft of the cap being perpendicular to the top flat surface of the substrate (the nail or base portion) for the washer to seal properly. In other words, the axis of the shaft of the cap must be aligned or coincident with the central axis of the hole in the nail.

SUMMARY OF THE INVENTION

The present invention provides an orthopaedic implant assembly including a securing member or screw and sealing washer assembled thereto. The assembly further includes a base member with a hole therein for receiving the screw and washer. The screw includes an enlarged head with an arcuate undersurface with a groove surrounding head for receiving the sealing washer therein. The screw hole includes a complementary arcuate surface to enable the screw to be inserted in a selectively variable angled orientation with respect to the screw hole while the washer provides a seal between the head of screw and the base member. The assembly may further include an additional member, such as an articulating surface, over the hole and screw and washer, such that this layer generates wear debris. The sealing washer provides a barrier to the advancement of the wear debris or particulate matter beyond the sealing washer.

Accordingly, it is an advantage of the invention to provide a screw and sealing washer in which the washer can maintain a secure seal while allowing the screw to be inserted at multiple angles relative to the base member or relative to the screw hole.

Another advantage of the invention is to advantageously provide the washer in a groove on a curved undersurface of the head.

A further object of the invention is to provide a novel seal for any desired sealing purpose between a securing member and a corresponding base member.

A still further advantage of the invention is to provide a seal between a screw and base support in which an additional load bearing member is also provided over the hole and screw in the base member such that the seal provides a barrier to the advancement of wear debris or particulate matter beyond the seal.

Still other advantages of the invention will become apparent upon reference to the accompanying drawings.

BRIEF DESCRIPTION OF THE DRAWINGS

FIG. 1 is a perspective view of an orthopaedic implant assembly in accordance with the present invention.

FIG. 2 is a fragmentary side view of the screw and washer shown in partial cross-section.

FIG. 3 is a perspective view of the washer.

FIG. 4 is a partial cross-sectional view of the base member and additional layer with the screw and washer inserted therein.

FIG. 5 is a partial cross-sectional view of the base member and additional layer with the screw and washer inserted therein with the screw at an alternate angular position with respect to the hole in the base member.

FIG. 6 is a partial cross-sectional view of an alternate embodiment of the base member and additional layer with the screw and washer inserted therein.

FIG. 7 is a partial cross-sectional view of an alternate embodiment of the base member and additional layer with the screw and alternate style of sealing washer inserted therein.

FIG. 8 is a perspective view of the alternate sealing washer of FIG. 7.

DESCRIPTION OF THE PREFERRED EMBODIMENT

The preferred embodiment described herein is not intended to be exhaustive or to limit the invention to the precise form disclosed. Rather, it is chosen and described to best explain the invention so that others skilled in the art might utilize its teachings.

Accordingly, FIGS. 1–5 illustrate the preferred embodiment of an orthopaedic implant assembly i in accordance with the present invention. The invention will be described with reference to a prosthetic tibial implant component as shown in FIG. 1. However, it is understood that the invention is not limited thereto, and that the features of the invention could be adapted to other orthopaedic implant assemblies.

FIG. 1 illustrates an orthopaedic implant assembly 1 in the form of a tibial implant component. This assembly 1 includes a base member or tibial plate 30 which is affixed to the tibial bone 50 via a plurality of screws 10. An additional member or articulating tibial surface 40 is located on the base member 30. Additional member 40 may be positioned on the base member 30 in any suitable manner, and may be mechanically secured thereto, if desired. Numerous ways of positioning and/or securing such additional members 40 are well known in the art of orthopaedics. Base member 30 may include a suitable porous surface 38, if desired, as is well-known in the art.

Screw 10 includes a sealing washer 20 assembled thereto. Screw 10 includes an enlarged head 11 with an elongated shaft 12 extending therefrom. The shaft includes screw threads 13 thereon. The head 11 includes an arcuate undersurface 14 with a groove 15 surrounding head 11 for receiving sealing washer 20 therein. The shaft 12 of screw 10 includes a central axis "A." Groove 15 may suitably be substantially perpendicular to axis "A."

Sealing washer 20 is resilient and flexible which enables the central opening 22 of washer 20 to stretch or expand slightly to fit over the head 11 of screw 10 and then snap into the groove 15. The preferred material for washer 20 is UHMWPE, however any suitable material such as a silicone ring or other suitable implantable material which would accomplish the desired sealing effect may be utilized. The washer 20 protrudes from groove 15 as shown in FIG. 2 by protruding portion 26. The flexibility of the material advantageously allows washer 20 to deform as shown in FIGS. 4 and 5 between the screw 10 and the base member 30 to provide a sealing contact therebetween when the screw 10 and washer 20 are inserted through base member 30 so that the threads 13 of screw 10 engage bone 50.

The protruding portion 26 of washer 20 may suitably be about 1 mm. The depth 16 of groove 15 may also be about 1 mm. The central opening 22 of washer 20 is sized appropriately to enable the washer 20 to stretch over the head 11 and yet securely fit into groove 15. This dimension would be adjusted as desired depending upon the size/dimensions of the head 11. The thickness 24 of the substantially cylindrical washer 20 may be about 0.875 mm while the height 17 of groove 15 may be about 1 mm. While these dimensions are identified as appropriate, it is noted that they are not considered limiting, as any suitable dimensions and sizing features may be utilized as desired to provide the desired sealing effect between the screw 10 and base member 30.

The base member 30 includes a plurality of holes 31 for receiving screws 10 with washers 20. The holes 31 include a complementary arcuate surface 34 to enable the screw 10 to be inserted in a selectively angled orientation with respect to the screw hole 31, while the washer 20 provides a sealing contact between the head 11 of screw 10 and the base member 30. The flexibility of sealing washer 20 enables sealing contact to be maintained between the screw 10 and the arcuate surface of the base member 30 at a plurality of angular positions. A bore 32 may extend from the arcuate surface 34. The bore 32 may be conical as shown in FIGS. 4 and 5, or cylindrical as shown in the alternate embodiment of FIG. 6. The diameter of the cylindrical shaped bore 32 of FIG. 6 is larger than the diameter of shaft 12 of screw 10 to allow for the angulation of the screw. The conical shaped bore 32 of FIGS. 4 and 5 allows even greater angulation of the screw 10 through bore 32.

It is known to provide screw fixation for tibial plates such as base member 30, and to provide for angulation of the screws. This angulation may be up to 10 to 15 degrees or more depending upon the desired component design. However, it is a significant advantage of this invention to provide a seal for such screws and to be able to maintain such seal even with the angulation of the screw. FIG. 4 shows the sealing contact of washer 20 with the screw 10 inserted so that central axis "A" of the screw 10 is coincident with central axis "B" of hole 31. FIG. 5 shows the sealing contact of washer 20 with the screw 10 inserted so that axis "A" of screw 10 is at an angle "AA" to axis "B" of hole 31.

The arcuate undersurface 14 of screwhead 11 and the complementary arcuate surface 34 of hole 31 of base member 30 are portions of mating spherical surfaces. These mating spherical surfaces may be in contact over at least a portion of the mating spherical surfaces as shown in FIGS. 4 and 5 to help distribute the load, while the washer 20 maintains sealing contact between screw 10 and base member 30. However, it is noted that the assembly 1 could be designed so that only the sealing washer engages between screw 10 and base member 30, and thus there is no physical contact between screw 10 and base member 30 as shown in the alternate embodiment of FIG. 6. Even though there is no direct contact between screw 10 and base member 30, the screw head 11 and hole 31 would still preferably include the mating or complementary spherical surfaces, as shown in FIG. 6, to allow the screw 10 to be angled with respect to hole 31. Since screw 10 and base member 30 may be made of surgical metals, such as a titanium alloy or cobalt-chrome alloy, if there was only engagement at washer 20 between screw 10 and base member 30, this would reduce the incidence of fretting which can occur due to the contact of the metal surfaces. It is noted, however, that any suitable materials may be utilized for screw 10 and base member 30.

The additional member 40 is a tibial articulating surface in the embodiment shown in the Figs. The additional member 40 is located on base member 30, and while additional member 40 may be positioned relative to the base in any suitable manner, in the embodiment shown, the additional member is mechanically affixed or secured to base member 30 by a suitable attachment mechanism (not shown), so that additional member 40 is positioned over screw holes 31 and the inserted heads 11 of screws 10.

The additional portion is preferably made of ultra high molecular weight polyethylene (UHMWPE), although any suitable material may be utilized. This polyethylene articulating surface 40 is typically mated with a femoral knee component (not shown) which may be made of metal such as a titanium or cobalt chrome alloy, or any other suitable material. The articulation of the femoral component on the tibial articulating surface 40 generates polyethylene wear debris or particulate matter over time. The sealing washer 20 provides a barrier to the advancement of this particulate beyond the sealing washer 20. This is advantageous because when this particulate passes through the screw hole 31, it can cause bone lysis which is not desirable.

It is also noted that over time, the tibial plate or base member 30 may subside slightly or migrate downward on the tibial bone 50, while the screws 10 remain in a fixed position in the bone. This can cause some separation or gap between the mating arcuate surfaces 14 and 34. However, since the sealing washer 20 is resilient and protrudes from groove 15, the washer 20 can accommodate this slight movement (which may be about 1 mm or less), while still maintaining sealing contact between screw 10 and base member 30.

As mentioned previously, the protruding portion 26 extending beyond head 11 may be up to about 1 mm or even greater (as desired) to accommodate the possible subsidence of plate or base member 30, as well as accommodate the desired angulation of screw 10.

It is noted that the principles of this invention are applicable to any suitable orthopaedic implant assembly, and may utilize at least one or may use a plurality of securing members, such as screws 10. It is also noted that the sealing washer 20 could be provided in the base member 30 so that it extends from screw hole 31, rather than from screw 10 (not shown). Thus, washer 20 could be positioned in a groove surrounding hole 31, so that it extends therefrom to provide the sealing contact between screw 10 and base member 30 when the screw 10 is inserted into bone 50 through base member 30.

FIGS. 7–8 illustrate a further alternate embodiment of the invention in which an alternate sealing washer 200 can be inserted into hole 31 to seal the hole after screw 10 has been inserted therethrough. The sealing washer 200 is positioned in hole 31 between screw 10 and additional member 40. In this embodiment the washer 200 seals the hole without surrounding the screw head, yet still allows the screw to be angled in hole 31. The sealing washer 200 is solid to prevent particulate or other materials from passing through hole 31. Sealing washer 200 may be secured to the hole 31 in any suitable manner to provide sealing of hole 31. One such suitable way is to thread washer 200 with threads 210 into mating threaded engagement with hole 31. The solid washer 200 may include a suitable recess for engaging a tool (not shown) to insert washer 200 into hole 31.

It is also noted that a seal could be provided between any two components for which a seal would be advantageous. For example, a sealing ring (not shown) could be provided directly between the additional member 40 (such as the articulating tibial surface) and the base member 30 (such as the tibial plate), if desired, rather than in cooperation with the screw hole 31 as shown in FIGS. 1–8.

While this invention has been described in terms of a particularly advantageous embodiment, those skilled in the art can appreciate that modifications can be made without departing from the spirit and scope of this invention.

I claim:

1. A method of providing a barrier to the advancement of wear debris in an orthopaedic implant assembly comprising the following steps:
    a) first locating a base member having at least one hole therein against a bone surface;
    b) then inserting a securing member through the at least one hole in a selectively angled orientation with respect to the at least one hole and directly into the bone surface to secure the base member to the bone and sealing the at least one hole; and
    c) subsequently positioning an additional member onto the base member such that the additional member covers the at least one hole; whereby the step of sealing the at least one hole provides a barrier to the advancement of wear debris from passing through the at least one hole, and wherein the step of sealing the at least one hole is achieved by providing the securing member with an enlarged head for seating against a complementary head receiving surface in the at least one hole and providing a sealing washer between the head and the complementary head receiving surface to seal the at least one hole.

2. The method of claim 1 wherein the method further includes providing the head of the securing member with a groove thereabout for receiving the sealing washer therein.

3. A method of providing a barrier to the advancement of wear debris in an orthopaedic implant assembly comprising the following steps:
    a) first locating a base member having at least one hole therein against a bone surface;
    b) then inserting a securing member through the at least one hole to secure the base member to the bone and sealing the at least one hole; and
    c) subsequently positioning an additional member onto the base member such that the additional member covers the at least one hole; whereby the step of sealing the at least one hole provides a barrier to the advancement of wear debris from passing through the at least one hole, and wherein the step of sealing the at least one hole is achieved by providing the securing member with an enlarged head for seating against a complementary head receiving surface in the at least one hole and providing a sealing washer between the head and the complementary head receiving surface to seal the at least one hole, and wherein the method further includes the step of providing the head of the securing member with an arcuate undersurface and further providing the complementary head receiving surface with an arcuate surface, wherein the securing member can be inserted in a selectively variable angled orientation with respect to the at least one hole while still maintaining the sealing of the at least one hole.

4. A method of providing a barrier to the advancement of wear debris in an orthopaedic implant assembly comprising the following steps:
    a) first locating a base member having at least one hole therein against a bone surface;
    b) then inserting a securing member through the at least one hole in a selectively angled orientation with respect to the at least one hole and directly into the bone surface to secure the base member to the bone and sealing the at least one hole; and
    c) subsequently positioning an additional member onto the base member such that the additional member covers the at least one hole; whereby the step of sealing the at least one hole provides a barrier to the advancement of wear debris from passing through the at least one hole, and wherein the at least one hole includes an opening between the inserted securing member and the additional member, and wherein the step of inserting the securing member and sealing the at least one hole comprises first inserting the securing member to secure the base member and then subsequently sealing the opening of the at least one hole by sealingly covering the opening after the screw has been inserted, and prior to positioning the additional member.

* * * * *